US008709399B2

(12) United States Patent
Vidal et al.

(10) Patent No.: US 8,709,399 B2
(45) Date of Patent: Apr. 29, 2014

(54) BIO-PESTICIDE AND METHOD FOR PEST CONTROL

(75) Inventors: Stefan Vidal, Goettingen (DE); Tadele Tefera, Orsay Cedex (KE)

(73) Assignee: Georg-August-Universität Göttingen Stiftung Öffentlichen Rechts, Göttingen (DE)

( * ) Notice: Subject to any disclaimer, the term of this patent is extended or adjusted under 35 U.S.C. 154(b) by 0 days.

(21) Appl. No.: 13/636,143

(22) PCT Filed: Mar. 24, 2011

(86) PCT No.: PCT/EP2011/054543
§ 371 (c)(1),
(2), (4) Date: Nov. 30, 2012

(87) PCT Pub. No.: WO2011/117351
PCT Pub. Date: Sep. 29, 2011

(65) Prior Publication Data

US 2013/0071425 A1 Mar. 21, 2013

(51) Int. Cl.

| | |
|---|---|
| ***A01N 63/00*** | (2006.01) |
| ***A01N 63/04*** | (2006.01) |
| ***A01N 65/00*** | (2009.01) |
| ***A61K 36/06*** | (2006.01) |
| ***A61K 36/09*** | (2006.01) |
| ***C12N 1/00*** | (2006.01) |
| ***A01H 9/00*** | (2006.01) |
| ***A01H 11/00*** | (2006.01) |

(52) U.S. Cl.
USPC ..................... 424/93.5; 424/195.15; 435/243; 435/254.1; 800/295

(58) Field of Classification Search
None
See application file for complete search history.

(56) References Cited

U.S. PATENT DOCUMENTS

| | | | | |
|---|---|---|---|---|
| 5,413,784 | A * | 5/1995 | Wright et al. | 424/93.5 |
| 5,759,562 | A * | 6/1998 | Rhodes et al. | 424/93.5 |
| 2002/0031495 | A1 * | 3/2002 | Morales et al. | 424/93.5 |
| 2008/0254054 | A1 * | 10/2008 | Jackson et al. | 424/195.15 |

FOREIGN PATENT DOCUMENTS

WO 2010/092223 8/2010

OTHER PUBLICATIONS

Shipp et al., Environmental Entomology, 32(5):1154-1163. 2003.*
Quesada-Moraga et al.; "Endophytic Colonisation of Opium Poppy, *Papaver somniferum*, by an Entomopathogenic *Beauveria bassiana* Strain"; Mycopathologia, vol. 161, No. 5, May 1, 2006, pp. 323-329.
Wagner et al.; "Colonization of Corn, *Zea mays*, by the Entomopathogenic Fungus *Beauveria bassiana*"; Applied and Environmental Microbiology, Aug. 1, 2000, pp. 3468-3473.
Tefera et al.; "Effect of inoculation method and plant growth medium on endophytic colonization of sorghum by the entomopathogenic fungus *Beauveria bassiana*"; Biocontrol, vol. 54, No. 5, Mar. 24, 2009, pp. 663-669.
Achonoduh et al.; "First report of pathogenicity of *Beauveria bassiana* RBL1034 to the malaria vector, *Anopheles gambiae* s.l. (Diptera; Culicidae) in Cameroon"; African Journal of Biotechnology, Apr. 17, 2008, pp. 931-935.
Scholte et al.; "Pathogenicity of five east African entomopathogenic fungi against adult *Anopheles gambiae* s.s. mosquitos (Diptera, Culicidae)"; Proc. Exper. Appl. Entomol., Jan. 1, 2003, pp. 25-29.

* cited by examiner

*Primary Examiner* — Chris R Tate
*Assistant Examiner* — Douglas F White
(74) *Attorney, Agent, or Firm* — Whitham Curtis Christofferson & Cook, PC

(57) ABSTRACT

The present invention relates to a new method for pest control and/or for preventing or treating pest infestation. Said method comprises the inoculation of plants, parts of plants or the surrounding of said plants with an effective amount of endophytic *Beauveria bassiana* strains. In a further aspect the present invention relates to the use of an isolated *Beauveria bassiana* strain having superior properties. Furthermore, biopesticides and compositions for pest control, in particular, for control of herbivorous insects and/or plant pathogens, are provided.

18 Claims, 1 Drawing Sheet

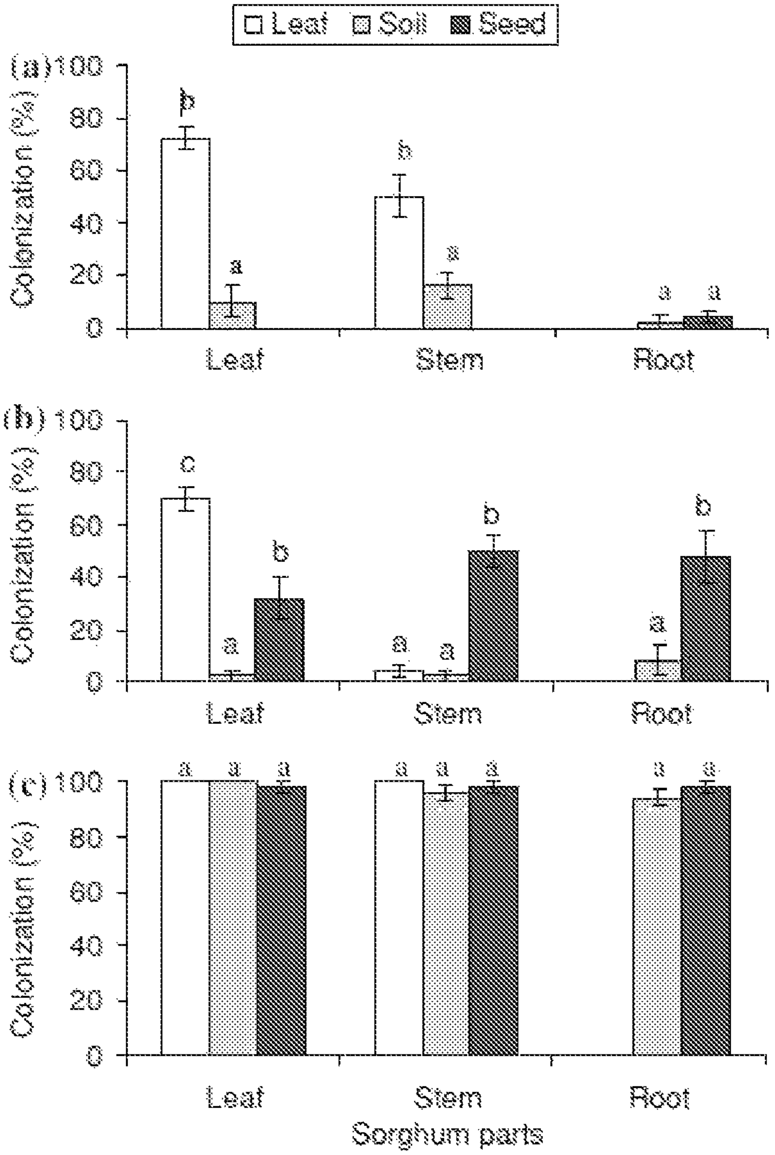
Leaf
Soil
Seed
(a)
(b)
(c)
Colonization (%)
100
80
60
40
20
0
Leaf
Stem
Root
Sorghum parts
a
b
c

BIO-PESTICIDE AND METHOD FOR PEST CONTROL

The present invention relates to a new method for pest control and/or for preventing or treating pest infestation. Said method comprises the inoculation of plants, parts of plants or the surrounding of said plants with an effective amount of endophytic *Beauveria bassiana* strains. In a further aspect the present invention relates to the use of an isolated *Beauveria bassiana* strain having superior properties. Furthermore, bio-pesticides and compositions for pest control, in particular, for control of herbivorous insects and/or plant pathogens, are provided.

PRIOR ART

The term endophyte, as was first introduced in 1866, broadly refers to any organism found within tissues of living autotrophs. A working definition for the term, later introduced by Petrini in 1991 and has since been widely accepted, defines endophytes as organisms that at some time in their life colonize internal plant tissues without causing apparent harm to their host. So defined, endophytes comprise a diverse polyphyletic group of microorganisms that can exhibit more than one type of life history at distinct life stages.

Although ubiquitous among all terrestrial plants Petrini O (1991) Fungal endophytes of tree leaves. In: Andrews J H, Hirano S S (eds), Springer-Verlag, New York, pp 179-197), the majority of endophyte research has focused to date on the vertically-transmitted endophytes within the genus *Neotyphodium* (Clavicipitaceae) that systemically colonize the aboveground parts of some grasses. These clavicipitaceous endophytes are generally known to confer an array of potential fitness benefits to their grass host. Less attention has, on the other hand, been given to the horizontally-transmitted non-clavicipitaceous endophytes, which are widespread in nature and dominated by Ascomycota. These endophytes represent at least three distinct functional groups that have been recovered from asymptomatic tissues of a wide variety of plants and have shown a broad scale of diversity in ecological roles and potential applications (reviewed in Rodriguez R, et al., (2009) New Phytol 182:314-330).

Emerging as an exciting new area of research, “fungal entomopathogens as endophytes” has been rather recently incorporated into an over 100-year-old endophyte research following the recovery of various genera of fungal entomopathogens as endophytes from different plant species. Some of these fungi have been reported as naturally occurring endophytes, while others have been introduced into the plant using different inoculation techniques (reviewed in Vega F E (2008), J Invertebr Pathol 98:277-279). Pioneer work on entomopathogenic endophytes was conducted with *Beauveria bassiana* (Balsamo) Vuillemin (Ascomycota: Hypocreales), a ubiquitous soil-borne fungus that is bioactive against a wide insect host range (>700 insect species) and one of the most commercialized fungal biopesticide. Lewis L C, Cossentine J E (1986), Entomophaga 31:36-69) credited the season-long suppression of the European corn borer *Ostrinia nubilalis* (Hübner) (Lepidoptera: Pyralidae) in maize *Zea mays* L. (Poaceae), measured as reduced tunnelling by the insect, to the establishment of *B. bassiana* as an endophyte following application of an aqueous suspension of the fungus to the plants. Subsequent work by Lewis and colleagues using the same model system indicated successful re-isolation of *B. bassiana* from plant internal tissues after application of the fungus with different inoculation methods and examined the in planta growth and movement of the fungus.

In addition to maize, a variety of host plants (including both agronomic and weedy species) have also been shown to harbour *B. bassiana* as an endophyte. Endophytic *B. bassiana* has been reported in the bark of ironwood *Carpinus caroliniana* Walter (Betulaceae), in potato *Solanum tuberosum* L. (Solanaceae), cotton *Gossypium hirsutum* L. (Malvaceae), common cocklebur *Xanthium strumarium* L. (Asteraceae), jimsonweed *Datura stramonium* L. (Solanaceae), cocoa *Theobroma cacoa* L. and its relative *Theobroma gileri* Coatrec. (Malvaceae), in seeds and needles of western white pine *Pinus monticola* Dougl. ex. D. Don, in pharmaceutical opium poppy *Papaver somniferum* L. (Papaveraceae), date palm *Phoenix dactylifera* L. (Arecacea), coffee *Coffea arabica* L. (Rubiaceae), tomato *Lycopersicon esculentum* (Solanaceae), banana *Musa* spp. (Musaceae) and sorghum *Sorghum* spp. (Poaceae) (Tefera and Vidal 2009). An establishment of *B. bassiana* as an endophyte has never been shown in oilseed rape *Brassica napus* L. (Brassicaceae) or *Vicia faba* L. (Fabaceae); or in either family for that matter.

In the art, *Beauveria bassiana* strain ATCC74040 is described as available tool for the control of pests, e.g. of the cherry fruit fly. Said *Beauveria bassiana* strain ATCC74040 is commercialised as the bio-pesticide “Naturalis” by Troy Biosciences. It is described as being useful for use with field crops, vegetables and fruits. At present, said product is used as standard bio-pesticide.

Further, *Helicoverpa armigera* (Hubner) (Lepidoptera: Noctuidae) is one of the most important insect pest in the world due to its mobility, high polyphagy, short generation time and high reproductive rate. Currently the application of insecticides is the most common practice of controlling this pest on crops including broad bean, cotton and chickpea. *H. armigera* is known to develop resistance to almost all the insecticides used for its control. The use of insecticides is also of environmental concern and is responsible for human health problems. Therefore, alternative control methods should be made available to users.

The females of *H. armigera* lay eggs on the underside of leaves, and first instar larvae feed on leaf whorls on young leaves. Second instar larvae penetrate the stem tissues to feed internally, producing extensive tunnels in stems. After excavating emergence windows to facilitate the exit of moths, the second instar larvae pupate in the tunnels. Control of these pests has been based on application of chemical insecticides but insecticides have limited effectiveness because of the cryptic feeding of these pests.

Among other, the objectives of the present invention are: (1) to examine for the first time the ability of *B. bassiana* to endophytically colonize *B. napus* and *V. faba* after being artificially introduced into plants, (2) to investigate whether plant colonization by fungus would differ among different host plants, and (3) to determine the potential of endophytic *B. bassiana* as a biocontrol agent against insect pests by confirming that the fungus still acts as a true insect pathogen after being introduced into plants. For this purpose, the virulence of endopyhtic *B. bassiana* was tested against *Helicoverpa armigera* (Hubner) (Lepidoptera: Noctuidae). The potential of the fungus when endophytic to confer virulence against *H. armigera* has never been previously investigated.

That is, the present invention aims to provide new methods for pest control as well as new bio-pesticides and compositions for pest control.

SUMMARY OF THE PRESENT INVENTION

In a first aspect, a method for pest control comprising an inoculation of plants, parts of plants or the surrounding of said plants within an effective amount of endophytic *Beauveria bassiana* strains, in particular, of *Beauveria bassiana* strain ATP02 deposited with the DSMZ, Braunschweig, Germany under the Budapest Treaty on Mar. 17, 2011 (DSM 24665) is provided.

Further, the present invention relates to the use of a new isolated *Beauveria bassiana* strain ATP02 and bio-pesticides as well as compositions containing said *Beauveria bassiana* strain as an active component for pest control.

DESCRIPTION OF THE DRAWINGS

FIG. 1: Mean (±SE) percent colonization of sorghum leaves, stems, and roots by *Beauveria bassiana* as affected by inoculation method (leaf, seed, or soil inoculation) of plants grown in a) non-sterile soil, b) sterile soil and c) vermiculite.

DETAILED DESCRIPTION OF PRESENT INVENTION

The present invention relates to the use of endophytic fungi, in particular *Beauveria bassiana* in compositions and methods of production and application for insect control. In particular, the use of the endophytic fungi *Beauveria bassiana* is useful in the field of plant protection, in particular as bio-pesticide. That is, the present inventors recognized that *Beauveria bassiana* allows endophytic colonization of various plants, in particular, *Vicia faba*, maize, broad bean, sorghum and, importantly, tobacco and rapeseed. Hence, the present invention relates in the first aspect to compositions useful as bio-pesticides for protecting the above identified plants and, in particular, agricultural crops against pests. For example, endophytic colonization of *Vicia faba* or *B. napus* by compositions containing *Beauveria bassiana* is useful for protecting against the pest *Helicoverpa armigera.*

Moreover, tobacco and rapeseed as well as maize and sorghum represents crops accessible to endophytic colonization by *Beauveria bassiana*. Particularly useful is the *Beauveria bassiana* strain ATP02 identified in the text and deposited on Mar. 17, 2011 with the DSMZ, Braunschweig, Germany, under the Budapest Treaty.

In particular, it has been recognized that treating the crops with endophytic *Beauveria bassiana* strains allows to impart a substantially life long colonization with *Beauveria bassiana* and, consequently, a substantially life long protection of crops colonized with said endophytic fungi. In addition, the present application relates to methods for protecting plants, in particular, agricultural crops, comprising the step of inoculation or coating of leaf, seed, soil, stems, branches, and roots, in particular, coating or inoculation of seeds with endophytic *Beauveria bassiana* strains, thus, preferably providing a substantially life long colonization with said endophytic *Beauveria bassiana* and, consequently, resulting in protection of said crops against pests.

The *Beauveria bassiana* strains are applied as follows, but not limited to, foliar sprays, stem injections, soil drenches, immersion, root dipping, seed coating or encapsulation using known techniques.

The crops are particularly selected from *Vicia faba*, rapeseed, chickpea, maize, sorghum, broad bean, cotton, and tobacco but also include soy, banana, coffee, tomato, cacao, cabbage, corn, bean, potato, opium poppy, date palm, pine, wheat, rice, and cereals, respectively.

Hence, the present application relates to a method for insect control comprising applying to the locus of said insects an insecticidally effective amount of the *Beauveria bassiana* strains allowing endophytic colonization of the plants invaded with said insects.

For example, the use of *Beauveria bassiana* allows controlling *Helicoverpa armigera* in *Vicia faba* and *B. napus.*

*Beauveria bassiana* may be provided in form of solutions, dispersions, sclerotia, gel, layer, cream, coating, dip, etc. The endophytic colonization of said entomopathogenic fungi allows providing a more stable and sustained protection against pests than non-endophytic colonization of said crops. That is, in contrast to bio-pesticides provided only on the surface of said crops, the endophytic colonization is more resistant against environmental factors like UV-light and is more stable and is resistance against removal by rain. Moreover, the endophytic property of the fungi allows growing with the crops and, hence, the treatment of the crops at the seed stage is sufficient to impart a substantially life long protection.

Preferred embodiments relate to the use of *Beauveria bassiana* compositions as bio-pesticides for protection of rapeseed, maize, chickpea and tobacco whereby *Beauveria bassiana* compositions are inoculated during the seed stage. In addition, sorghum may be treated with the entomopathogenic fungus *Beauveria bassiana*. Thus, *Beauveria bassiana* allows protecting said plants against herbivorous insects and plant pathogens.

In addition, the present invention provides a method for controlling one or more phytopathogenic pests, e.g. insects, comprising the step of applying to a plant, parts of plants or its surroundings a composition containing an effective amount of *Beauveria bassiana.*

That is, in a first aspect the present invention relates to a method for pest control comprising inoculation of plants, parts of plants or the surrounding of said plants with an effective amount of endophytic *Beauveria bassiana* strains, in particular, of *Beauveria bassiana* strain ATP02.

In particular, the present inventors recognised that the *Beauveria bassiana* strain ATP02 is useful for pest control and demonstrated superior properties over known bio-pesticides based on *Beauveria bassiana* strains.

That is, the *Beauveria bassiana* strain ATP02 is superior in its properties regarding colonisation of the plants, in particular of the crops. In addition, the mortality data, the mucosis and the survival time of the pests are superior when treated with ATP02 in comparison to know products. Hence, it is particular preferred that the *Beauveria bassiana* strain is ATP02.

In another embodiment, the present invention relates to a method for treating or preventing plants against pest infestation comprising the step of inoculation of the plants, parts of said plants or the surroundings of said plants with an endophytic *Beauveria bassiana* strain, in particular, with the *Beauveria bassiana* strain ATP02.

It is particular preferred that the plant, parts of plants or the surrounding of said plants is selected from leaf, seed, branches, soil, stems, roots. It is particular preferred that seeds are inoculated or coated with the *Beauveria bassiana* strain. In a preferred embodiment, said inoculation is achieved by coating said seeds with spores, conidia or microsclerotia of the *Beauveria bassiana* strain.

That is, treatment of the plants may be effected by coating the seeds or any other part of said plants or, alternatively, bringing the *Beauveria bassiana* strain into close contact with the plants or part of said plants, e.g. by seed coating, spraying, immersing, dipping, injecting, drenching, spraying or encapsulation.

As outlined in more detail below, the *Beauveria bassiana* strain may be in form of a dispersion or spore solution, sclerotia, emulsion, gel, layer, cream, coating, dip, encapsulated, or granules.

It is preferred that the plants to be treated or inoculated with the endophytic *Beauveria bassiana* strain are crops. It is particularly preferred that said crops are selected from *Vicia faba*, rapeseed, chickpea, maize, sorghum, broad bean, cotton, tobacco, soy, banana, coffee, tomato, cocoa plants, corn, bean, potato, opium poppy, date palm, pine, wheat, rice, cereals, barley plants etc.

Moreover, it is particular preferred that the plants are selected from rapeseed, *Brassica napus*, cotton, maize, corn and soy.

In another preferred embodiment, the method for pest control is a method wherein the pests are insects. In particular, it is preferred that the pests are herbivorous insects and/or plant pathogens. Typical examples of herbivorous insects and plant pathogens according to the present invention are *Helicoverpa armigera, Plutella xylostelle, Trialeurodes vaporariorum*, or *Spodoptera exigua. Helicoverpa armigera* also known as cotton bollworm or corn earworm is a highly polyphagous species. The most important crop hosts are tomato, cotton, pigeon pea, chickpea, sweet pepper, and cowpea. Other hosts include groundnut, okra, peas, field beans, soybeans, alfalafa, bush beans, potatoes, maize, flax, *Dianthus, Rosa, Pelargonium, Chrysanthemum*, a number of fruit trees, forest trees and a range of vegetable crops. In Russia and adjacent countries, the larvae populate more than 120 plant species, favouring *Solanum, Datura, Hyoscyamus, Atriplex* and *Amaranthus* genera.

The greatest damage is caused to cotton, tomatoes, maize, chickpeas, alfalfa and tobacco. The economic threshold of harmfulness in central Asia is three to five larvae per hundred plants of long-staple cotton and eight to twelve larvae per hundred plants on medium-staple cotton. In cotton crop, blooms that have been attached may open prematurely and stay fruitless, when the boss are damaged, some will fall off and others will fail to produce lint or produce lint of an inferior quality. Secondary infections by fungi and bacteria are common and may lead to rotting of fruits. Injury to the growing tips of plants may disturb their development, maturity may be delayed and the fruits may be dropped. Control measures include the growing of resistant varieties, weeding, inter-row cultivation, removing crop residues, deep autumn ploughing, winter watering to destroy the pupae, the use of insecticides or biological control through the release of entomophages such as *Trichogramma* spp. and *Habrobracon hebetor*. Monitoring is possible by the use of sex pheromone traps.

The term “insecticide” refers to a material or mixture of materials which induce mortality, disrupt or impede growth, interfere with metamorphosis or other morphogenic function, effect sterilisation, or interfere with reproduction of the targeted insects. The terms “controlling” or “control of the target insect” is used herein to mean that the population of the insect is reduced, principally through mortality, at a level that is significantly greater than an untreated population, i.e. with significant mortality.

“Significant mortality” is defined herein to mean that the percentage of insects that die within a given period of time after coming into contact with the insecticide is significantly greater than the number of insects not contacted with the insecticide that die during the same period of time, based on standard statistical analyses.

Commercial formulations for use as a biological insect control agent may be prepared from *Beauveria bassiana* that have been harvested from culture medium. As a practical matter, it is envisioned that commercial formulations may be prepared directly from the culture, thereby obviating the need for any purification steps. While liquid cultures may be used directly, in the preferred embodiment the water is removed from the cultures to partial or substantial dryness as described above, and the dried culture broken or ground into small particles suitable for application through conventional granule applicators, using techniques conventional in the art. To facilitate application and subsequent fungal outgrowth and, if necessary, conidiation, the harvested *Beauveria bassiana* may alternatively be formulated in a suitable, agronomically acceptable, nutritional or inert carrier or vehicle for application as wettable powders, dusts, granules, baits, solutions, emulsifiable concentrates, emulsions, suspension concentrates and sprays (aerosols). For example, for liquid applications, the *Beauveria bassiana* may be formulated as a suspension or emulsion. In this embodiment, preferred carriers include but are not limited to water, buffers, or vegetable or plant oils. In an alternative, preferred embodiment particularly suited for solid granular applications, the *Beauveria bassiana* may be formulated with solid inert carriers or diluents such as diatomaceous earth, talc, clay, vermiculite, $CaCO_3$, corn cob grits, alginate gels, starch matrices or synthetic polymers, or they may be incorporated into conventional controlled release microparticles or microcapsules. The skilled practitioner will recognize that the fungi may also be formulated in combination with conventional additives such as sticking agents or adherents, emulsifying agents, surfactants, foams, humectants, or wetting agents, antioxidants, UV protectants, nutritive additives, fertilizers, insecticides, or even with fungicides which exhibit low toxicity to the subject fungi.

The absolute amount of the *Beauveria bassiana* and their concentration in the final composition are selected to provide an effective reduction in the population of the target insect as compared to an untreated control. The actual amount is not critical and is a function of practical considerations such as the properties of the vehicle or carrier, the density of the target insect population, and the method and site of application, and may be readily determined by routine testing. An “effective amount” is defined to mean any quantity of *Beauveria bassiana* sufficient to subsequently establish endophytic colonization in the target habitat allowing eventually infection and killing the target insect relative to an untreated control. By way of example and without being limited thereto, it is envisioned that suitable formulations will typically contain about $1\times10^6$ or higher *Beauveria bassiana* per gram of biomass recovered from the liquid culture (based on the dried weight of the biomass), preferably at least $1.5\times10^7$ *Beauveria bassiana* per gram of biomass, Of course, the skilled person will determine the effective amount based on the formulation of the composition.

In use, the *Beauveria bassiana* of this invention may be applied to the potential locus or vicinity of the target insects e.g. on the surface of the plants to be protected, like, onto tree bark, or as a seed coating, using conventional techniques. In another preferred embodiment, the *Beauveria bassiana* are applied to the soil, or to soil-less potting mixes such as are used in greenhouses, in a granular form. The *Beauveria bassiana* are applied in a way to allow endophytic colonization of the target plants.

The *Beauveria bassiana* of this invention are effective in infecting and killing a wide variety of economically important insects, particularly, but without being limited thereto, soil-born insects, but also including some ground- and canopy-dwelling insects. Without being limited thereto, insects which may be controlled by the *Beauveria bassiana* of this invention include root weevils, rootworms, wireworms, maggots, bugs, aphids, beetles, root weevils, borers, fruit flies, soil grubs, root maggots, termites, and ants, particularly corn rootworm (*Diabrotica* spp.), black vine weevil (*Otiorhynchus sulcatus*), citrus root weevil (*Diaprepes abbreviatus*), sweet potato weevil (*Cylas formicarius*), sugarbeet root maggot (*Tetanops myopaeformis*), cabbage maggot (*Delia radicum*), onion maggot (*Delia antigua*), turnip maggot (*Delia floralis*), seedcorn maggot (*Delia platura*), carrot rust fly (*Psila rosae*), Japanese beetle (*Popillia japonica*), European chafer (*Rhizotrogus majalis*), coffee berry borer (*Hypothenemus hampei*), stem borer (*Chilo partellus*), subterranean termite (*Reticulitermes* and *Coptotermes* spp.). In addition, certain canopy dwelling, especially bark dwelling, insects may be controlled by *Beauveria bassiana* of this invention. These insects include, but are not limited to, emerald ash borer (*Agrilus planipennis*), gypsy moth (*Lymantria dispar*), and the pecan weevil (*Curculio caryae*).

In another preferred embodiment, the present invention relates to a bio-pesticide containing *Beauveria bassiana* ATP02. In particular, the bio-pesticide is suitable as bio-pesticide against herbivorous insects or other pests, as detailed in the following:

maize pests: Corn earworm (*Helicoverpa zea*), Fall armyworm (*Spodoptera frugiperda*), Common armyworm (*Pseudaletia unipuncta*), Stalk borer (*Papaipema nebris*), Corn leaf aphid (*Rhopalosiphum maidis*), European corn borer (*Ostrinia nubilalis*) (ECB), Corn silkfly (*Euxesta stigmatis*), Lesser cornstalk borer (*Elasmopalpus lignosellus*), Corn delphacid (*Peregrinus maidis*), Western corn rootworm (*Diabrotica virgifera virgifera* LeConte), Southwestern corn borer (*Diatraea grandiosella*), Maize weevil (*Sitophilus zeamais*)

rapeseed pests: Meligethes aeneus, Harlequin bug (*Murgantia histrionica*), Flea beetles (*Phyllotreta* sp.), Diamondback moth (*Plutella xylostella*), Bertha armyworm (*Mamestra configurata*), Root maggot (*Delia* sp.), Grasshoppers, Lygus bugs (*Lygus* spp.), Bronzed field beetle larvae, Snails and slugs.

cotton pests: Boll weevil, cotton bollworm pink bollworm (*Pectinophora gossypiella*); the chili thrips (*Scirtothrips dorsalis*), and the cotton seed bug (*Oxycarenus hyalinipennis*).

Cacao pests: Cocoa pod borer (*Conopomorpha cramerella*), cocoa mirids or capsids Wheat pests: The Flame (*Axylia putris*), Rustic shoulder-knot (*Apamea sordens*), setaceous, hebrew character (*Xestia c-nigrum*), Turnip moth (*Agrotis segetum*).

Sorghum pests: *Chilo partellus, Busseola fusca, Sesamia calamistis.*

The bio-pesticide may be in a form of a solution, a dispersion, a spray, gel, emulsion, layer, cream, coating, dip, encapsulated or granule.

Further, the present invention relates to a composition containing *Beauveria bassiana* strains ATP02 as an active component for pest control, in particular for control of herbivorous insects and plant pathogens.

Finally, the present invention relates to the use of *Beauveria bassiana* strain ATP02 for endophytic colonisation of plants, in particular for colonization of plants for preventing or treating pest. It is preferred that the *Beauveria bassiana* strain ATP02 is used for the colonisation of *Vicia faba*, maize or corn, broad bean, sorghum, tobacco, rapeseed, soy, chickpea, cotton, banana, coffee, tomato, pine, potato, rice, cereals, wheat, cocoa plants for pest control.

The following examples are intended only to further illustrate the invention and are not intended to limit the scope of the invention that is defined by the claims.

EXAMPLES

Example 1

Materials and Methods

Fungus

The experiments used strain ATP02 of *B. bassiana*, which had been isolated from the maize stem borer *B. fusca* at the Haramaya University, Ehtiopia. This fungal strain was selected based on its virulence to the spotted stem borer *C. partellus* according to the methods as described in previous studies for other strains (Tefera and Pringle, 2004, Biocon Sci Technol, 14, 849-853). Fungus cultures were maintained at 25° C. on Sabouraud dextrose agar (SDA), containing 10 g enzymatic digest casein, 40 g dextrose, and 15 g agar. Conidia were obtained from 3-week-old sporulating cultures. The conidia were harvested by scraping the surface of the culture with a sterile camel hairbrush into a 500 ml glass beaker containing 50 ml sterile distilled water plus Tween 80 (0.1% v/v; Difco™). The conidial suspension was prepared by mixing the solution with a magnetic stirrer for 5 min. The conidia concentration was then adjusted to the desired concentration of $1\times10^8$ conidia $ml^{-1}$ with a Thoma Chamber using a light microscope (40× magnifications). To assess viability of the conidia, germination test was carried out on SDA after incubation for 24 h at 23° C. The germination exceeded 90%. A suspension of $1\times10^8$ conidia $ml^{-1}$ was used in the experiments. The conidia concentration $1\times10^8$ conidia $ml^{-1}$ was chosen based on virulence of the isolate to *C. partellus* at this concentration (Tefera and Pringle 2004, above).

Sorghum Plants

The experiments used the sorghum cultivar P9403, commonly called "Abshir", from the Haramaya University, Ethiopia, released by Purdue University (USA) to east Africa due to its resistance to witchweed (*striga* sp.), a parasitic plant. Although it is widely grown in different agronomic regions of Ethiopia, where the grain is used for human consumption and the crop residue is used for animal feed, P9403 is susceptible to stem borers. As described in the following paragraphs, the sorghum was inoculated with *B. bassiana* in one of the three ways (by inoculating seeds, leaves, or soil), and the inoculated plants were grown in one of three media (vermiculite, sterile soil, or non-sterile soil).

Experiment I: Effect of Inoculation Method on Colonization of Sorghum by *B. bassiana*

Seeds were surface sterilized by submerging them in 3% sodium hypochlorite for 3 min and then in 75% ethanol for 2 min; the seeds were then rinsed in sterile water three times. The treated seeds were placed on sterile filter papers to dray for 30 min before being divided into two portions. The first portion was used for seed inoculation while the second portion was used for leaf and soil drench inoculations after seedling emergence. The seeds intended for leaf and soil inoculation were planted in pots filled with approximately 2 kg of sterile potting soil (autoclaved at 121° C. for 15 min), non-sterile potting soil, or vermiculite. The plants were maintained in the greenhouse at 21-22° C., 60-80% RH, and with a 12 h photoperiod. Four seeds were planted per pot and were thinned to two seedlings after emergence.

For seed inoculation, 50 g seeds were immersed into 10 ml *B. bassiana* conidial suspension ($1\times10^8$ conidia $ml^{-1}$) for 10 min. After the inoculated seeds were dried on sterile tissue paper for 30 min, they were planted in pots as described in the previous paragraph. However, the exact rate of conidia that was attached to the seeds was not determined. Control seeds were immersed in sterile distilled water. For leaf inoculation, a plastic hand sprayer (500 ml capacity) was used to inoculate each seedling with a 3 ml conidial suspension ($1\times10^8$ conidia $ml^{-1}$) seven days after emergence. The spray was directed to the leaves but might have incidentally drifted to the stems. To avoid conidial runoff to the soil, the top of each pot was covered with aluminum foil. The control plants were inoculated with sterile distilled water. For soil inoculation, a 3 ml conidial suspension ($1\times10^8$ conidia $ml^{-1}$) was applied around the root zone of each seedling. The control plants were inoculated with 3 ml sterile distilled water. Seedlings in all treatments were watered as needed. To avoid conidial runoff from the treated leaves to the stem and soil, watering device was carefully directed to the surface of the pot.

Separate experiments were conducted using non-sterile soil, sterile soil, and vermiculite. Within each experiment, a completely randomized block design with ten replicates per treatment (inoculation method) was used.

Experiment II: Effect of Plant Growth Medium on Colonization of Sorghum by *B. bassiana*

We conducted an experiment to determine the effect of the three plant growth media (Vermiculite, sterile soil, or non-sterile soil), on colonization of sorghum by *B. bassiana*, using the seed inoculation method. Non-treated seeds were included as a control for each plant growth medium. A complete randomized block design with ten replicates was used. We followed the same treatment application procedures and experimental management as described above in experiment I for the seed inoculation.

Data Collection and Statistical Analysis

Colonization

Colonization of sorghum seedlings by *B. bassiana* was determined 20 days after inoculation with *B. bassiana*. Seedlings were carefully removed from pots, and roots were gently washed with tap water. The seedlings were then separated into leaves, stems, and roots. These parts were surface-sterilized with 1% sodium hypochlorite for 3 min, rinsed twice in sterile distilled water, and then placed on sterile tissue paper in a laminar flow cabinet. Five leaf, stem and root pieces of approximately 2 $mm^2$ from each seedling were randomly taken and placed separately on *B. bassiana* selective medium (2% oatmeal infusion, 2% agar, 550 $\mu g\ ml^{-1}$ dodine, 5 $\mu g\ ml^{-1}$ crystal violet). To evaluate the efficacy of the surface sterilisation method 20 ml of the water used to rinse the tissues after surface sterilisation was taken and 20 μl aliquots of a $10^{-3}$ dilution were plated on the selective media and spread with a sterile glass rod, incubated for ten days at 22±2° C. to count for colony forming units. However, the sterilizsation resulted in no growth of microorganisms, thus any enuing *B. bassiana* growth from surface-sterilized tissues is inferred to have originated from internal plant tissues as endophytes. The presence or absence of *B. bassiana* growth on the pieces was recorded after ten day at 20-23° C. A total of 120 plants and 600 plant pieces were examined in experiment I, while a total of 60 plants and 180 plant pieces were examined in experiment II. The data were expressed as colonization frequencies: colonization frequency=100×(number of plant pieces colonized/total number of plant pieces) (Petrini and Fisher, 1987, Trans British Mycol Soc, 87, 87, 647-651). The colonization frequency data (expressed as percentages) were angular transformed to stabilize the variances. The transformed data were analyzed using analysis of variances (ANOVA) of the program SPSS Version 16. Significant differences between means were determined with the Student-Newman-Keuls test (P=0.05).

Plant Growth

The effect of the fungus on plant growth (Experiment I) was determined by measuring shoot height, root length, and shoot and root fresh weight 35 days after inoculation of the plants with the fungus. Plant height was measured from the soil surface to the tip of the stem. After shoot fresh weight, root fresh weight (roots had been washed to remove soil), and root length were recorded, the fresh shoots and roots were placed in a paper bag and kept at 45° C. for six days before dry weights were determined. The plant growth data were subjected to one-way ANOVA using the SPSS Version 16. Significant differences between means were determined with the Student-Newman-Keuls test (P=0.05).

Results

Experiment I: Effect of Inoculation Method on Colonization by *B. bassiana* and the Growth of Sorghum No *B. bassiana* was recorded from the control plants growing in non-sterile soil, sterile soil, or vermiculite. For sorghum growing in non-sterile soil, inoculation method significantly affected the colonization of leaves ($P<0.01$; $F_{2,27}=73.61$) and stems ($P<0.01$; $F_{2,27}=22.53$) but not roots ($P=0.35$; $F_{2,27}=1.08$) by *B. bassiana* (FIG. 1*a*). Leaf and stem colonization were highest with leaf inoculation, lower with soil inoculation, and non-detectable with seed inoculation. Root colonization was much lower than leaf and stem colonization. Although the differences were not significant, root colonization was highest with seed inoculation, lower with soil inoculation, and non-detectable with leaf inoculation.

For sorghum growing in sterile soil, inoculation method significantly affected the colonization of leaves ($P<0.01$; $F_{2,27}=40.68$), stems ($P<0.01$; $F_{2,27}=50.62$), and roots ($P=0.35$; $F_{2,27}=15.77$) by *B. bassiana* (FIG. 1*b*). Leaf inoculation resulted in the highest leaf colonization, while seed inoculation caused the highest stem and root colonisation. Regardless of plant part colonized, colonization by *B. bassiana* of sorghum growing in sterile soil was low with soil inoculation.

For sorghum growing in vermiculite, inoculation method significantly affected colonization of roots ($P<0.01$; $F_{2,27}=692.1$) but not of leaves and stems by *B. bassiana* (FIG. 1*c*). Colonization was greater than 90% with all inoculation methods and plant parts except that colonization was 0% with leaf inoculation of roots.

Within each experiment (i.e., for each growth medium), plant height, fresh weight, and dry weight were not significantly affected by inoculation method (table 1), i.e., inoculation of sorghum with *B. bassiana* did not reduce plant growth. Although statistical analysis could not be used to compare plant growth in different growth media, plant growth appeared to differ with growth media. Plants grown in vermiculite were much shorter and weighed less than plants grown in sterile or non-sterile soil.

Experiment II: Effect of Plant Growth Medium on Colonization of Sorghum by *B. bassiana*

We found significant differences with regard to the growth medium affecting leaf ($P<0.01$; $F_{2,27}=134.9$), stem ($P<0.01$; $F_{2,27}=469.4$) and root ($P<0.01$; $F_{2,27}=228.9$) colonization of sorghum by *B. bassiana* (table 2), espectively. Growing *B. bassiana* treated seeds in non-sterile soil did not result in leaf and stem colonization, and root colonization by the fungus was limited. However, when sorghum seeds were grown in sterile soil and vermiculate, fungal colonization was observed in leaf, stem and root parts. Colonization was higher for seeds grown in vermiculite as compared to sterile soil. No *B. bassiana* was recorded from the control plants.

TABLE 2 effect of plant growth medium on sorghum leaf, stem and root colonization by *B. bassiana*

| | Plant parts colonized (%) | | |
|---|---|---|---|
| Growth medium | Leaf | Stem | Root |
| Non-sterile soil | 0 ± 0a | 0 ± 0a | 16 ± 2.7a |
| Sterile soil | 32 ± 5.3b | 40 ± 5.9b | 48 ± 3.2b |
| Vermiculite | 92 ± 5.3c | 100 ± 0c | 100 ± 0c |

Means (±SE) followed by the same letter within a column are not significantly different at $P < 0.05$ Discussion This study demonstrates that *B. bassiana* can be established as an endophyte in sorghum leaves, stems, and roots by inoculating leaves, seeds, or soil. However, the level of colonization seemed to be substantially affected by plant growth medium. Although the effect of growth medium on plant colonization by the fungus has not been previously considered, successful colonization of many plant species following inoculation with *B. bassiana* has been reported previously. Endophytic colonization by *B. bassiana* however, depended upon the inoculation method, fungal isolate, and plant species. For example, the highest post-inoculation recovery of *B. bassiana* occurred after direct injection in coffee, dipping plants in conidial suspension in banana tissue culture, foliar application in opium poppy and maize, and seed coating in tomato.

In the current study, *B. bassiana* colonization differed among the plant parts. Leaves and stems were colonized to a greater extent than roots. The colonization of the different plant parts indicate that the fungus moves within the plant system. The reason for higher colonization of leaves and stems is not clear but could reflect differences in microbial and physiological conditions in the different plant parts. Petrini and Fisher (1987) reported that endophytic fungi exhibited tissue specificity because they are adapted to particular conditions present in a given plant part.

Planting conidia-treated seeds in vermiculite and sterile soil, rather than in non-sterile soil, improved endophytic colonization of *B. bassiana*. Autoclaving the soil might have eliminated microorganisms that otherwise would have competed with or antagonized *B. bassiana*. However, seed and soil inoculation methods did not significantly increase in endophytic colonization by the fungus in non-sterile soils, compared to leaf inoculation method. The reason for the lack of endophytic colonization in seeds treated with *B. bassiana* in non-sterile soil is not clear and requires further investigation. Abiotic and biotic soil factors, however, were reported to affect occurrence of the entomopathogenic fungus *Beauveria brongniartii* after application at different times of the year. The low endophytic colonization of the fungus in non-sterile soil suggests that biotic factors may have a stronger influence on the fungus than abiotic factors. Fungistatic effects of soil and soil antagonism have been reported for *B. bassiana*. In the non-sterile soil, biotic antagonism may have inhibited germination of *B. bassiana* conidia or prevented the fungus from penetrating roots. For instance, the common soil fungus *Penicillium urticae* produces a water soluble inhibitor of *B. bassiana*. Another common soil saprophyte, *Aspergillus clavatus*, also produces metabolites that are fungicidal to *B. bassiana*. It has been reported that *B. bassiana* had a low persistence in soils and that the fungus infected only a small proportion of insects when conidia were added directly to the soil.

Plant growth was affected by the growth medium (sterile oil, non-sterile soil, and vermiculite) but not by the inoculation method. Plant growth in vermiculite was much less than in sterile and non-sterile soil, regardless of the inoculation method. No differences in growth between plants treated or not treated with *B. bassiana* have been reported. In the current study, seed treatment with *B. bassiana* did not reduce seed germination or seedling growth, and did not result in the development of root disease. Application of *B. bassiana* to leaves, seeds, or soil did not result in significant differences in plant height, fresh weight, or dray weight. Although differences in plant growth and dry weight were evident when plants were grown in vermiculite, sterile soil, and non-sterile soil, these differences apparently did not affect colonization of the plants by *B. bassiana*.

The endophytic colonization of sorghum by *B. bassiana* suggests that this isolate is well adapted to a wide range of conditions including endophytic in plants and pathogenic to insects. *B. bassiana* can become established as an endophyte in sorghum without adversely affecting plant growth, and leaf inoculation with a conidial suspension proved to be the best method to introduce *B. bassiana* into sorghum leaves. This study provides the basis for further investigations, which should focus on the response of different sorghum cultivars to different strains of *B. bassiana*, the long term establishment throughout the entire life of the inoculated plants, and the virulence of the endophytic *B. bassiana* against sorghum stem borers. An application technology should be developed that protects *B. bassiana* conidia against soil antagonism in order to maximize endophytic colonization by the fungus in non-sterile soil.

Example 2

Materials and Methods

Fungal Strains and Conidia Preparation

The experiments used strain ATP02 of *B. bassiana* for testing their ability to endophytically colonize plants and their pathogenicity against third instar *H. armigera* larvae. Strain ATP02, endophytically colonizing the plant, was tested for possible effects on mortality and growth of *H. armigera*. The fungal strain had been isolated from *H. armigera* and *Busseola fusca*, respectively, at the Haramaya University, Ethiopia. The fungal strain was selected based on their efficacy in endophytic colonization (100%) of sorghum, see above. Fungus cultures were maintained at 25° C. on Sabouraud dextrose agar (SDA), containing 10 g enzymatic digest casein, 40 g dextrose, and 15 g agar. Conidia were obtained from 3-week-old sporulating cultures. The conidia were harvested by scrapping the surface of the culture with a sterile camel hairbrush into a 500-ml glass beaker containing 50 ml sterile distilled water plus Tween 80 (0.1% v/v) (Difco™). The conidial suspension was prepared by mixing the solution with a magnetic stirrer for 5 minutes. A drop of Tween 80 (Difco) was then added to the beakers containing sterile-distilled water and conidia. The conidia concentration was adjusted to the desired concentration using a Thoma Chamber under a light microscope (400× magnifications) following the procedure described by Goettel and Inglis (1997). Prior to each bioassay, the viability of conidia was checked by carrying out a germination test. A droplet of conidia suspension ($1\times10^{-4}$ conidia $ml^{-1}$) was pipetted onto the plate, covered with a thin cover slip, and incubated at 22-23° C. for 12 hr. The plate was examined using a light microscope (Olympus BH-2, Olympus Optical Co. Ltd., Japan) 400× magnification. One hundred conidia were examined at three locations on each plate and scored as either germinated (viable) or not germinated (dead). Conidia were considered to have germinated when the germ tube was at least as long as the width of the germ tube. The germination of conidia exceeded 90% in all bioassays.

Insect

Eggs of *H. armigera* were obtained from Bayer CropScience AG, Monheim, Germany. The eggs were incubated at 22° C. until hatching. The newly hatched neonate larvae were reared on bean flour based artificial diet prepared following the procedure described by Teakle (1991). The larvae were kept on the diet at conditions of 22° C., 70% RH and 14L:10D photoperiod until the third instar stage.

Experiment-I: Pathogenicity Test

In order to test for the efficacy of the *B. bassiana* ATP02 strain against *H. armigera*, third instar larvae reared on the artificial diet were used. A batch of 60 larvae per strain was immersed into 20 ml conidial suspension in a Petri dish containing $1\times10^8$ conidia for 30 s. The exact amount of conidia attached to the body of the larvae was, however, not determined. The treated larvae were transferred, using a clip-on cage, to a 3-week old *V. faba* seedlings grown in a greenhouse chamber, and maintained at 22±2° C., 70% RH, and a photoperiod of 14L:10D. Mortality was monitored daily and dead larvae were removed and placed onto Petri dishes lined with moist filter paper to encourage mycosis of the cadavers. Survival time (days) of each larva was recorded. Mortality and mycosis data were expressed as percentage of total sample. Mortality, mycosis and survival time were analyzed using one-way analysis of variances.

Experiment II: Effect of Endophytic *B. bassiana* Atp02 Strain on the Mortality and Growth of *H. armigera*

Planting and Inoculation

In this assay, we determined endophytic colonization of *V. faba* by *B. bassiana* ATP02 strain and the effect of strain ATP02 on the mortality and growth of *H. armigera. V. faba* seedlings (cultivar, Hangdown Grünkernig, Gevo GmbH,) were grown in a greenhouse chamber. Two-week-old plants were individually transplanted into plastic pots (11 cm diameter) with a mixture of sand and soil (1:1 ratio). The plants were monitored daily and watered when needed. Three weeks after seedling emergence, the third leaf pair (both upper and lower side), was sprayed with 3-ml of $1\times10^8$ conidia $ml^{-1}$ of each strain using a plastic hand sprayer (500-ml capacity). Third leaf pairs of the control plants were sprayed with the same amount of sterile distilled water.

Larval Growth and Mortality (Strain ATP02)

This part was carried out using *B. bassiana* strain ATP02. Prior to introducing larvae to the plants treated with endophytic *B. bassiana* strain ATP02, leaf samples were randomly taken from the treated plants to determine if conidia survived on the leaf surfaces. The leaves were rinsed into a sterile distilled water containing a drop of Tween-80 for 3-min. The suspension from the leaf washing was then pipetted onto the *B. bassiana* selective media and incubated at 22±2° C. for seven days in darkness. No colony forming units were observed. Ten days after the plants were treated with the fungus, a third instar larva was introduced to the ATP02-inoculated and control plants using a clip on cage (3.5 cm diameter). One larva was used per plant and a total of 30 larvae (30 plants) were used per treatment, each larva (plant) considered as a replicate, in a completely randomized design. The larval feeding site of the leaves was changed when required. Mortality was monitored daily and dead larvae were removed and placed onto Petri dishes lined with moist filter paper to encourage mycosis of the cadavers. Mycosed cadavers were recorded. A cadaver is regarded to have mycosed when an external growth of the fungus on the insect cuticle is confirmed. Two and four days after introduction of the larvae to inoculated and control plants, the larvae were removed from clip-on cages, and the weight of each larva was recorded, the larvae were then placed back onto their original host plant. Larval weight gain was expressed as the difference between the initial and final weight assessment; and was calculated as a percentage of the initial weight. The relative growth rate (RGR) was calculated as follows: RGR=ln [(W2−W1)/(t2−t1)].

Where; =ln is the base natural logarithm; $W_1$ is the initial weight; $W_2$ is the final weight; $t_2$ and $t_1$ are the time of final and initial weight assessment, respectively (Needham and Lerner, 1940, Nature, 146, 618). Mortality, mycosis, larval weight, and RGR were analyzed using one-way analysis of variance.

Recovery of *B. bassiana* from Inoculated Plants

At the end of the experiment, ten plants were randomly selected from each treatment to assess the colonization of *V. faba* seedlings by *B. bassiana*. Third leaf pairs were randomly sampled per plant, surface-sterilized with 1% sodium hypochlorite for 3 min, rinsed twice in sterile distilled water, and then placed on sterile tissue paper in a laminar flow cabinet. Five leave pieces of approximately 2-$mm^2$ from each leaf pair were randomly cut, placed separately on *B. bassiana* selective medium (2% oatmeal infusion, 2% agar, 550 μg/ml dodine, 5 μg/ml crystal violet), and incubated at 22±2° C. The presence or absence of *B. bassiana* growth on the tissue pieces was recorded 15 days post-incubation. To evaluate the efficacy of the surface sterilization method, 20-ml of the water used to rinse the tissues after surface sterilization was taken and 20-ml, aliquots of a $10^{-3}$ dilution were plated on the selective media, spread with a sterile glass rod, and incubated for 10 d at 22±2° C. to assess for colony forming units. However, the sterilization resulted in no growth of microorganisms. Any ensuing *B. bassiana* growth from surface-sterilized tissues was, thus, inferred to have originated from internal plant tissues. A total of 30 plants and a 150 plant pieces were examined. Since there was no colonization in the control plants, it was excluded from the analysis. The data were expressed as colonization frequency: colonization frequency=100×(number of plant pieces colonized/total number of plant pieces) (Fisher and Petrini, 1987, above). The colonization data (expressed as percentages) were analyzed using one-way analysis of variance.

Experiment III: Effect of Endophytic *B. bassiana* on Growth of *V. faba*

We set up an experiment to determine the effect of endophytic *B. bassiana* (ATP02) on growth of *V. faba*. Seedlings of *V. faba* were obtained and treated with the fungal strains as described above in Experiment-II. Treatments consisted of the two strains and a control. The treatments were arranged in a completely randomized design and replicated 10 times. The effect of the fungus on plant growth was determined by measuring shoot height, shoot fresh and dry weight 15 days after inoculation of the plants with the fungus. Plant height was measured from the soil surface to the tip of the stem. After shoot fresh weight were recorded, the fresh shoots was placed in a paper bag and kept at 45° C. for 6 days before dry weight was determined. The plant growth data were subjected to one-way analysis of variances using the SPSS Version 16. Significant differences between means were determined using Tukey's HSD test (P=0.05).

Results

Experiment I: Pathogenicity Test

There was no control mortality and hence mortality was not adjusted for the control. Larvae suffered the highest mortality (100%) when treated with the strain ATP02. High mycosis (100%) was recorded from larvae treated with ATP02. The survival time of larvae when treated with ATP02 was significantly low (4.3 days).

Experiment II: Effect of Endophytic *B. bassiana* (Strain Atp02) on Mortality and Growth of *H. armigera*

Larvae fed on endophytic ATP02 suffered high mortality (86%) and mycosis (86%) as opposed to zero mortality and mycosis in the control. There was no difference in larval initial weight (F=1.660; df=1.59; p=0.23); however, there were significant differences in larval final weight (F=168.429; df=1.59; p<0.01) and percent weight gain (F=14.863; df=1.59; p<0.01) between *H. armigera* larvae feeding on *V. faba* endophytically colonized by ATP02 and the control (table 3).

TABLE 3

Mean initial and, final weight and percent weight gain of *H. armigera* larvae feeding on *V. faba* endophytically colonized by *B. bassiana* (BB-04) and the control plants.

| | Weight of larvae (mg) | | |
|---|---|---|---|
| Treatment | Initial | Final | % weight gain |
| ATP02 | 3.1 ± 0.2a* | 12.0 ± 0.9a | 650.8 ± 95.9a |
| Control | 3.9 ± 0.5b | 49.7 ± 2.7b | 1449.9 ± 183.7b |

*Mean ± SE values followed by the same letter within a column are not significantly different at 5%.

There was about 55.1% weight loss in the larvae feeding on endophytic ATP02 treated plants as compared to the control. There were also significant differences (F=23.563; df=1, 59; p<0.01) between the treatments in relative growth rate of the larvae. Larvae feeding on plants endophytically colonized by *B. bassiana* had reduced growth rate than the larvae feeding on the control plants. We observed no colonization of control plants by *B. bassiana*; however, colonization of *V. faba* leaves treated with the fungus was 100%.

Experiment III: Effect of Endophytic *B. bassiana* on Growth of *V. faba*

Plant height, fresh and dry shoot weight were not significantly affected by inoculation of plants with the *B. bassiana* strain (table 4), i.e., inoculation of *V. faba* with *B. bassiana* did not reduce plant growth.

TABLE 4

Effect of endophytic *B. bassiana* strains on growth of *V. faba*.

| Strain | Shoot height (cm) | Fresh weight (g) | Dry weight (g) |
|---|---|---|---|
| APT02 | 64.4 ± 1.8a | 21.4 ± 0.9a | 2.1 ± 0.08a |
| Control | 62.9 ± 1.7a | 20.7 ± 0.5a | 2.1 ± 0.09a |

* Mean ± SE values followed by the same letter within a column are not significantly different at 5%.

Discussion

Our study demonstrated that both direct immersion treatment of *H. armigera* larvae with the fungus and feeding the larvae with plants colonized by *B. bassiana* caused the highest mortality. We reported for the first time the establishment of *B. bassiana* in *V. faba* as an endophyte inducing larval mortality and reduced weight gain. Other studies on artificial use of *B. bassiana* as an endophyte revealed that colonization of maize by the fungus reduces tunneling caused by *Ostrinia nubilalis, Sesamia calamistis* and reduction of the banana weevil by *C. sordidus.*

*H. armigera* larvae feeding on endophytic *B. bassiana* colonized plants gained less weight than those feeding on the control plants. Pathogen-induced behavioral changes may affect insect feeding and consequently lead to less weight gain and abnormal growth.

Mortality may be attributed to production of toxic substances by the fungi and/or mechanical disruption of the insect's structural integrity by hyphal growth. The destructive effects of the pathogen's proteases on insect cuticle including the gut have been reported. Further, it was indicated that secondary metabolites produced by *B. bassiana* are among the primary factors affecting virulence of the fungus to second instars of *H. armigera*. In the present study, *B. bassiana* strain ATP02 caused mortality as well as reduction in growth by *H. armigera*. If as a consequence of fungal infection, larval growth and feeding is reduced, it should be considered from a biological control viewpoint. Insect pathogens often require several days to kill their hosts. During this period, the insects may continue feeding, adding to crop damage before their death. However, food consumption by insects can be reduced when they are infected. Therefore, infection with entomopathogenic fungi can bring a degree of control of damage resulting from reduced food consumption. Thus, effective control need not be determined by mortality alone.

Endophytic *B. bassiana* (strain ATP02) might have produced toxins inside the plant tissue that retarded feeding and development of *H. armigera* larvae, consequently resulting in reduced food consumption and growth rate. In the present study, all larvae died as a result of feeding on endophytic plant profusely sporulated on the surface of the cadavers confirming the activity of the endophytic ATP02 strain against *H. armigera* was through direct parasitism. Our work revealed that the pathogenicity of the fungus against the larvae was not affected when the fungus was established as an endophyte inside plant tissues.

Innoculation of leaves with *B. bassiana* (strain ATP02) did not result in significant differences in plant height, shoot fresh weight, or dry weight. Tefera and Vidal (2009) reported no differences in growth between plants treated or not treated with *B. bassiana.*

In conclusion, strain ATP02 of *B. bassiana*, which was originally isolated from the maize stem borer *B. fusca*, endophytically colonized *V. faba* in the current study suggesting the potential of this strain in colonizing different hosts. *B. bassiana* can be established as an endophyte in broad bean without adversely affecting plant growth. Future study should focus on the long-term establishment of the fungus and production of toxic metabolites in the plant tissues; and interaction of endophytic *B. bassiana* with natural enemies of *H. armigera.*

Example 3

Materials and Methods

Plants

Oilseed rape *B. napus* (cultivar Favorite, DSV-Deutsche Saatveredelung, Lippstadt, Germany) and broad bean *V. faba* (cultivar Hangdown Griinkernig, Gevo GmbH, Nortmoor, Germany) seedlings were grown in a greenhouse chamber. Ten-day-old plants were individually transplanted into plastic pots (11 cm diameter) with a mixture of non-sterile soil (Fruhstorfer Erde Typ T, Hawita Gruppe GmbH, Vechta, Germany) and sand (1:1 ratio). Plants were irrigated regularly and fertilized once a week with 15:10:15:2 NPKMg (COMPO GmbH, Munster, Germany).

Insects

The egg masses of a laboratory strain of *H. armigera* were provided by Bayer Crop Science, Mohnheim, Germany and kept in a climatic chamber at 25° C., 60% RH and 14L:10D photoperiod until hatching. Neonate larvae were then reared on standard bean flour based artificial diet for *Helicoverpa* spp. (Teakle R E (1991) Laboratory culture of *Helicoverpa* spp., methods and prospects. Springer-Verlag, New York) until the second instar stage. Early second instar larvae were transferred from the artificial diet to leaves of *V. faba* plants (non-treatment plants) for habituation. Only larvae which successfully moulted to the third instar stage on *V. faba* plants were used in experiment II.

Fungal Isolates/Strains

Ten isolates of *B. bassiana* were screened for their ability of endophytic establishment in *B. napus* and *V. faba* (experiment I.). The isolates were sampled to constitute representatives from insect or plant hosts collected from different geographical regions (table 5). All isolates (except the active ingredient of the registered *B. bassiana*-based bioinsecticide Naturalis®) were maintained on respective recommended growth media under recommended environmental conditions. Only three of the screened *B. bassiana* isolates were reported to occur as endophytes, either naturally or artificially (table 5).

TABLE 5

Beauveria bassiana isolates/strains screened for endophytic establishment in *Brassica napus* and *Vicia faba*

| Isolate/strain[a] | Geographic origin | Insect host[b] | Plant host[c] (reference) |
|---|---|---|---|
| Bb03032 | Colombia | — | Coffee Coffee *arabica* L. Berries (N)[d] (Vega et al., 2008) |
| EABb04/01-Tip* | Spain | stem-borer *Timaspis papaveris* (Kieffer) larva | Opium puppy *Papaver somniferum* L. (I) (Quesada-Moraga et al., 2009), |
| ATP02 | Ethiopia | stem borer *Busseola fusca* (Fuller)) | *sorghum Sorghum* spp. (I) |
| Bb 64 | Austria | Codling moth *Cydia pomonella* L. larva | — |
| Bb101 | The Netherlands | Black vine weevil *Otiorhynchus sulcatus* (Fabricius) adult | — |
| Bb135 | Germany | European spruce bark beetle Ips *typographus* L. adult | — |
| Bb 1022* | Canada | Pine shoot moth *Rhyacionia buoliana* (Schiff.) | — |
| Bb1025* | Canada | Insect (unidentified= | — |
| Bb1555* | Canada | — | Dead leaf (unidentified) |
| Naturalis ® (strain ATCC74040-based bioinsecticide) | USA | Cotton boll weevil *Anthonomus grandis* (Boheman) | — |

[a]Only isolates that have been characterized by molecular or biological means from other studies are referred to as strains (marked with an asterisk)

[b]Insect host from which the isolate/strain was originally isolated

[c]Plant host on which the isolate/strain has been reported as endophyte

[d]An (N) or (I) following the host plant indicates whether *B. bassiana* was reported as a naturally occurring endophyte (N) or introduced into the plant via artificial inoculation (I)

Preparation of Conidial Suspensions and Viability Test

Conidia were obtained from 3-week-old sporulating cultures of all isolates/strains except Naturalis®, of which conidia were obtained directly from the biopesticide formulation. The conidia were harvested under sterile conditions by scraping them off the culture surface with a camel hairbrush into a 500-ml bottle containing 200 ml sterile distilled water plus Tween 80 (0.1% v/v, Difco™). The conidial suspension of each isolate/strain was then mixed with a magnetic stirrer for 5 min to homogenize the hydrophobic conidia. Conidial concentration for each isolate/strain was determined under the microscope using an improved Neubauer hemocytometer and adjusted to a concentration of $1\times10^8$ conidia $ml^{-1}$, which was used in all of the following experiments. This conidial concentration was sufficient for some of the *B. bassiana* isolates/strains used in our study to endophytically colonize other host plants in previous studies (Posada F, et al., 2007, Mycol Res 111:749-758). Conidial viability was tested for each isolate/strain by carrying out a germination test. A low concentration of conidia was suspended in 0.1% Tween 80 solution and a 20 μl aliquot from this stock was plated onto SDA medium. The aliquot was spread with a sterile glass rod onto the medium surface and incubated at 25° C. for 24 h. Spore germination was checked under the microscope. Three groups of 100 conidia selected at random were assessed for germination. Only spores with a germ tube as long as the conidium widths were considered to have germinated.

Experiment I. Screening *B. bassiana* Isolates/Strains for Endophytic Establishment in *B. napus* and *V. faba*

The objective here was to examine the ability of a sample of *B. bassiana* isolates, collected from different insect or plant hosts originating from disparate geographical regions, to endophytically colonize *B. napus* and *V. faba* plants. Ten isolates/strains of *B. bassiana* were screened in an experiment that was planned with two main factors in a full-factorial design. The first factor was *B. bassiana* isolate/strain (see table 5) and the second factor was host plant (*B. napus* or *V. faba*). For each isolate/strain, a conidial stock suspension was prepared in sterile 0.1% Tween 80 solution and the spore concentration was adjusted to $1\times10^8$ conidia $ml^{-1}$ (as described above). A plastic hand sprayer was used to inoculate plants with the fungal conidial suspension and an average of 4 ml of the suspension was applied to the upper and lower surface of two opposite leaves assigned on each *B. napus* plant, and to the third leaf pair on each *V. faba* plant. Inoculation with an aqueous conidial spray was more effective than other inoculation methods in facilitating the endophytic establishment. Plants in the control treatment received the same amount of sterile 0.1% Tween 80 solution applied in the same manner. There was a total of 30 treatment combinations; each replicated 10 times (n=10). After inoculation, plants were randomized in blocks along a single greenhouse bench at 22±2° C., 60±10% RH, and 14L:10D photoperiod.

Seven days past-inoculation, plant colonization by different isolates/strains of *B. bassiana* was determined through re-isolation of the fungus from all inoculated leaves using the method described in (Arnold A E, et al., 2001, Mycol Res 105:1502-1507). *B. bassiana*-inoculated leaves were cut from all treatment plants and surface-sterilized by submerging in 0.5% sodium hypochlorite for 2 min, followed by 2 min in 70% ethanol and three rinses in sterile distilled water. Leaves were then allowed to surface-dry in the laminar flow hood. Twelve leaf discs (approximately 2 $mm^2$) per plant replicate were cut from surface-sterilized inoculated leaves using a sterile cork borer. Thus, a total of 120 leaf discs were obtained per treatment combination. Leaf discs were evenly plated onto *B. bassiana* selective medium (2% oatmeal infusion, 2% agar, 550 $\mu ml^{-1}$ dodine, 5 $\mu g\ ml^{-1}$ crystal violet) in 55 mm plastic Petri dishes. In order to determine whether the surface sterilization method was successful in eliminating epiphytic microorganisms, 20 µl aliquot from $10^{-3}$ dilution of the final rinse water was plated onto Petri dishes of selective medium. Petri dishes were sealed and incubated for two weeks at 25° C., after which all leaf discs were examined visually for fungal growth. Fungal growth was characterized as *B. bassiana* based on white dense mycelia, becoming cream to pale yellow at the edge. For each isolate/strain, percent colonization was calculated following the Petrini and Fisher (1987), see above, formula: % colonization=number of leaf discs showing *B. bassiana* outgrowth divided by the total number of incubated leaf discs×100.

Experiment II. Testing the Virulence of Endophytic *B. bassiana* Isolates/Strains Against *H. armigera*

This experiment was conducted in order to determine the potential of endophytic *B. bassiana* as a biocontrol agent of *H. armigera*. The virulence of endophytic *B. bassiana* against this insect pest was examined using *B. bassiana*-inoculated *V. faba* because it is reported as one of the host plant species for *H. armigera*. Only *B. bassiana* strains/isolates that were able to endophytically colonize *V. faba* plants in experiment I were used in this part of the study. For each isolate/strain, a conidial suspension was prepared in sterile 0.1% Tween 80 solution and the spore concentration was adjusted to $1\times10^8$ conidia $ml^{-1}$ (as described above). For inoculation, a plastic hand sprayer was used to apply the conidial suspension of each isolate/strain and an average of 4 ml per plant was sprayed on the upper and lower surface of the third leaf pair on each plant. Plants in the control treatment received the same amount of sterile 0.1% Tween 80 solution applied in the same manner. There was a total of 13 treatments, each replicated 20 times (n=20). After inoculation, plants were randomized in blocks along a single greenhouse bench at environmental conditions similar to that mentioned above (in experiment I).

Seven days past-inoculation, a clip-on cage containing a single early third instar *H. armigera* larva was attached to one of the leaflets of the non-inoculated fourth leaf pair on each plant in order to ensure that any virulence against the introduced larvae is ensuing from fungal growth within plant tissues (i.e. from endophytic *B. bassiana*). The larvae in all treatments were monitored daily and days to mortality (i.e. insect survival time) was recorded. In cases where almost all leaf material within the cage was consumed, the clip-on cage containing the larva was moved to the next leaflet of the fourth leaf pair and kept on the plant until death or pupation. Dead larvae were transferred to Petri dishes lined with moistened filter papers to promote outgrowth of the respective *B. bassiana* isolate/strain. Mycosis of larval cadavers (i.e. cadavers showing external mycelia growth) was monitored daily for 14 days.

In order to check for the successful inoculation of plants with *B. bassiana* in each treatment by the time *H. armigera* third instar larvae were introduced, endophytic establishment by the fungus was determined for all treatments seven days past-inoculation through re-isolation from surface-sterilized tissues of non-treatment plants that had been treated similarly to treatment plants.

Statistical Analyses

Raw data were checked for normality and homogeneity of variance using the Shapiro-Wilk test. Data on percent colonization of plants by *B. bassiana* as well as percent larval mortality and mycosis were arcsine transformed prior to analyses to meet assumptions of normality and homogeneity of variance. Percent colonization of plants by *B. bassiana* in experiment I was analyzed using two-way analysis of variance (ANOVA), with *B. bassiana* isolate/strain and host plant as main factors. Differences in percent colonization among treatment combinations were tested using Tukey's Honestly-Significant-Difference (HSD) test with Bonferroni correction for multiple testing. In experiment II, sets of one-way ANOVAs were used to analyze percent larval mortality, percent mycosis of cadavers, and larval survival time; followed by Tukey's HSD test with Bonferroni correction to separate treatment means when significant. All analyses were performed using SYSTAT for Windows, version 12 (SYSTAT 2008).

Results

Experiment I. Screening *B. bassiana* Isolates/Strains for Endophytic Establishment in *B. napus* and *V. faba*

Spore germination of all screened *B. bassiana* isolates/strains was more than 90%. Neither *B. bassiana* nor any other microorganism were ever observed in the final rinse water plated following surface-sterilization of plant tissues. Therefore, outgrowth of *B. bassiana* from surface-sterilized leaf discs originated from endophytic colonization of the plant tissues by the fungus. All screened *B. bassiana* isolates/strains were able to colonize inoculated leaves of *B. napus* and *V. faba*, except Bb101 and Bb1555 (Table 2). No outgrowth of the fungus was observed from either host plants inoculated with the conidial suspension of these two isolates/strains, or with the sterile 0.1% Tween 80 solution in the control treatment. However, percent colonization varied significantly among the screened isolates/strains within each host plant ($F_{14,270}$=70.060; P<0.0001; two-way ANOVA; Table 3). For example, colonization of *B. napus* by *B. bassiana* was significantly higher when the plants were inoculated with isolates/strains ATP02, and ATCC74040 (*B. bassiana*-based Naturalis®) in contrast to Bb03032, Bb1022, and Bb1025 (P<0.05; Tukey's HSD test with Bonferroni correction for multiple testing; Table 2). On the other hand, colonization of *V. faba* plants by ATP02 was significantly higher than that by Bb03032, and ATCC74040 (*B. bassiana*-based Naturalis®) (P<0.05; Tukey's HSD test with Bonferroni correction for multiple testing; table 6).

TABLE 6

Percent colonization of *Brassica napus* and *Vicia faba* plants by ten *Beauveria bassiana* isolates/strains seven days past-inoculation of plants with a sterile 0.1% Tween 80 conidial suspension containing $1 \times 10^8$ conidia $ml^{-1}$ of each isolate/strain. Plants in the control treatment were treated with sterile 0.1% Tween 80 solution. Colonization (%) represents the number of colonized segments divided by the total number of cultured segments × 100

| Treatment *Beauveria bassiana* | Colonization (%) ± SE | |
|---|---|---|
| isolate | *Brassica napus* | *Vicia faba* |
| ATP02 | 92.73 ± 2.27 A[a], a[b] | 91.82 ± 2.12 A, a |
| Bb03032 | 55.46 ± 5.50 A, c | 68.18 ± 7.33 A, b |
| EABb04/01-Tip | 71.82 ± 5.15 A, abc | 79.09 ± 5.43 A, ab |
| Bb64 | 70.91 ± 9.66 A, abc | 81.82 ± 3.03 A, ab |
| Bb 101 | 00.00 ± 0.00 d | 00.00 ± 0.00 d |
| Bb135 | 64.04 ± 7.67 A, be | 75.46 ± 3.85 A, ab |
| Bb1022 | 54.55 ± 3.83 A, c | 78.18 ± 4.54 B, ab |
| Bb1025 | 52.73 ± 4.66 A, c | 72.73 ± 7.55 B, ab |
| Bb1555 | 00.00 ± 0.00 d | 00.00 ± 0.00 d |
| Naturalis ® (strain ATCC 74040-based bioinsecticide) | 83.64 ± 2.27 A, ab | 68.18 ± 5.29 B, b |
| Control | 00.00 ± 0.00 d | 00.00 ± 0.00 d |

[a]Different uppercases indicate means (±SE) that are significantly different within rows (P < 0.05, Tukey's HSD test with Bonferroni correction for multiple testing after two-way ANOVA)

[b]Different lowercases indicate means (±SE) that are significantly different within columns (P < 0.05, Tukey's HSD test with Bonferroni correction for multiple testing after two-way ANOVA)

Moreover, there was an interaction between *B. bassiana* isolate/strain and host plant ($F_{14,270}$=2.898; P<0.0001; two-way ANOVA). Strain ATCC74040 (*B. bassiana*-based Naturalis®) colonized *B. napus* plants better than *V. faba* plants, while strains Bb1022 and Bb1025 colonized *V. faba* plants better than *B. napus* plants (P<0.05; Tukey's HSD test with Bonferroni correction for multiple testing; table 2).

Experiment II. Testing the Virulence of Endophytic *B. bassiana* Isolates/Strains Against *H. armigera*

Plant colonization by *B. bassiana* at the time of introduction of third instar *H. armigera* was confirmed by the successful re-isolation of the fungus from non-treatment plants inoculated with the tested isolates/strains, but not from control non-treatment plants. While all *H. armigera* larvae fed upon plants in the control treatment remained alive until pupation, larval mortality was observed on plants inoculated with the fungus in all other treatments; irrespective of the *B. bassiana* isolate used (table 4). However, only plants inoculated with the isolates ATP02, and Bb03032 resulted in a significantly higher larval mortality as compared to control plants (P<0.05; Tukey's HSD test with Bonferroni correction for multiple testing after one-way ANOVA; table 7). Whereas none of the larval cadavers collected from plants inoculated with isolate/strain BB1022 displayed *B. bassiana* mycosis, between 0 and 100% of the cadavers recovered from plants inoculated with the remaining isolates/strains showed mycosis (table 7). Survival time varied significantly among larvae fed upon plants inoculated with different *B. bassiana* isolates/strains ($F_{12,99}$=60.847; P<0.0001; one-way ANOVA). Isolate ATP02 caused significantly faster larval mortality as compared to the remaining isolates/strains (table 7).

TABLE 7

| Treatment | Parameter sampled ± SE | | |
|---|---|---|---|
| *B. bassiana* isolate | Mortality (%) | Mycosis (%) | Survival time (days) |
| ATP02 | 85.00 ± 0.08 a | 100.00 ± 0.00 a | 6.41 ± 0.58 a |
| Bb03032 | 55.00 ± 0.11 abc | 54.55 ± 0.16 a | 18.64 ± 0.64 c |
| EABb04/01-Tip | 45.00 ± 0.11 abcd | 66.67 ± 0.17 a | 19.11 ± 0.63 c |
| Bb64 | 40.00 ± 0.11 abcd | 50.00 ± 0.19 ab | 20.25 ± 0.59 c |
| Bb135 | 25.00 ± 0.10 bcd | 40.00 ± 0.25 ab | 20.80 ± 0.66 cd |
| Bb1022 | 30.00 ± 0.11 bcd | 00.00 ± 0.00 b | 21.00 ± 0.97 cd |
| Bb1025 | 35.00 ± 0.11 bcd | 28.57 ± 0.18 b | 20.29 ± 0.67 c |
| Naturalis ® (strain ATCC74040-based bio-insecticide) | 25.00 ± 0.10 bcd | 22.22 ± 0.15 b | 21.11 ± 0.68 cd |
| Control | 00.00 ± 0.00 d | 00.00 ± 0.00 b | 24.60 ± 0.83 d |

[a] For each sampled parameter, means (±SE) followed by the same letter within a column are not significantly different at P < 0.05 (Tukey's HSD test with Bonferroni correction for multiple testing after one-way ANOVA)

Discussion

All screened *B. bassiana* isolates used in this study, except Bb101 and Bb1555, were able to endophytically colonize both *B. napus* and *V. faba* after being artificially introduced into plants through foliar spray. The establishment of *B. bassiana* as an endophyte in *B. napus, V. faba*, or their respective plant families has never been demonstrated so far. A majority (11 out of 14) of the *B. bassiana* isolates screened here have never been previously reported as an endophyte in any host plant. Also interesting is the finding that the registered *B. bassiana*-based biopesticide Naturalis® was able to colonize both host plants following artificial inoculation as well. Significant differences were, however, observed in percent colonization by the endophytic isolates/strains within and between host plants. For example, although isolate ATP02 was the best colonizer of both *B. napus* and *V. faba* in contrast to other isolates/strains, some isolates/strains (e.g. ATCC74040-based Naturalis®) were better colonizers of *B. napus* compared to *V. faba* while others (Bb1022 and Bb1025) colonized *V. faba* better than *B. napus*. These results clearly demonstrate the generalist character of *B. bassiana* as an endophyte and corroborate the suggestion that *B. bassiana* occurrence in both monocotyledonous and dicotyledonous angiosperms as well as gymnosperms (see Introduction) indicates the potential of diverse plants to form endophytic association with this fungal entomopathogen (Vega, 2008, above) and recruit it as a bodyguard.

The bodyguard hypothesis, first introduced by (Price P W, et al., 1980, Annu Rev Ecol Evol Syst 11:41-65), suggests that plants can use insect natural enemies as bodyguards to protect themselves from herbivory. Since then, increasing evidence in support of this hypothesis has been yielded regarding insect predators and parasitoids, but not insect pathogens. In their review however, Elliot et al. (Elliot S L, et al., 2000, Ecol Lett 3:228-235) extended this hypothesis by arguing that plants can also use fungal entomopathogens as bodyguards in a similar way to recruiting other insect natural enemies. They proposed three possible mechanisms for such plant-bodyguard interaction; (1) maintaining a population of entomopathogens on the plant surface, (2) increasing contact rates between insect hosts and entomopathogens, and (3) increasing susceptibility of the insect host. Here we suggest a further mechanism: deliberately maintaining fungal entomopathogens in planta as endophytes. The ability of different *B. bassiana* isolates, originating from disparate insect/plant hosts collected from different climatic conditions, to colonize two different host plants as shown in our study lends credence to our suggestion. In fact, one of the most notable characteristics of fungal entomopathogens is that they exhibit a huge range of host specificity, ranging from very narrow for the obligate pathogens to very large for the facultative ones; to which various genera of fungal entomopathogens reported as endophytes belong (Vega, 2008). Such continuum of host range, and thus life history, for the facultative entomopathogens (including *B. bassiana*) could stem from their ability to acquire nutrients from sources other than insects; which ostensibly allows for interkingdom host-jumps from arthropods to plants and vice versa. *B. bassiana* displays various nutritional habits (e.g. parasitic, saprophytic and endophytic). The full details of such evolutionary switches among different types of nutritional habits remain unknown. However, natural selection may lead a fungus to nutritional adjustments to its environment and consequently force it to start using nutrients from different kingdoms. Fungal entomopathogens spend a significant period of time on the plant surface and are thus vulnerable to plant surface characteristics, exposure to damaging UV radiation and adverse changes in microclimate. Sheltering these fungi within plants adds to the novel ways in which plants could manipulate, fungal entomopathogens and modify their efficacy.

The failure to establish endophytic association with two of the tested isolates/strains might be due to innate characteristics of the fungal isolate/strain or host plant genetics, resulting in a unique outcome for each plant-genome-endophyte-genome interaction. Competition with other endophytes naturally occurring within plants could also lead to differential colonization rate of plants by different *B. bassiana* isolates/strains. On the other hand, the comparable colonization of inoculated and non-inoculated plant parts by the endophytic *B. bassiana* isolates/strains (as indicated by sampling of *V. faba* parts that were neither inoculated nor formed at the time of inoculation; LRJ et al. unpublished data) confirms that *B. bassiana* could move within plants. Despite such systemic colonization of plants by the fungus, neither adverse effects on growth nor symptoms have ever been observed in *B. bassiana*-colonized plants; even at inoculum rates as high as $1.5\times10^{10}$ conidia $ml^{-1}$. Similarly, *B. bassiana*-colonized plants in our study did not show any symptoms of disease or damage that might otherwise indicate that the fungus is deleterious to the plant. On the other hand, re-isolation of *B. bassiana* from inoculated-*V. faba* plants at locations distant from the point of inoculation shows that the hyphal growth and development of the fungus within plant tissues seemed not to be a limiting factor for its efficacy against *H. armigera*. However, only isolate ATP02 of the present invention was highly virulent against the insect in terms of all sampled parameters; resulting in a fast kill of the introduced larvae through direct parasitism as indicated by mycosis of all recovered cadavers. The lower efficacy of many of the tested endophytic *B. bassiana* isolates/strains against *H. armigera* may have been a function of their lower pathogenicity towards this insect in particular. Naturalis®, for example, is labeled as not being effective against lepidopteran pests and this might be the reason for its low efficacy against *H. armigera*.

Systemic protection by endophytic *B. bassiana* has been reported against *O. nubilalis* and *Sesamia calamistis* Hampson (Lepidoptera: Noctuidae) in maize, *Helicoverpa zea* Boddie (Lepidoptera: Noctuidae) in tomato, *Cosmopolites sordidus* Germar (Coleoptera: Curculionidae) in banana, and *Iraella luteipes* Thompson (Hymenoptera: Cynipidae) in opium poppy. Yet, the mechanisms underpinning endophytic *B. bassiana*-mediated protective effects remain little understood. Direct parasitism (indicated by mycosis) was only reported in *H. zea* larvae and *C. sordidus* larvae and pupae recovered from *B. bassiana*-inoculated tomato and banana plants, respectively; suggesting the presence of conidia as infective propagules (per os infection). Conidia were never detected inside *B. bassiana*-colonized plants though. Alternatively, *B. bassiana*-produced secondary metabolites were speculated to accumulate inside plant tissues and mediate the feeding deterrence or antibiosis of insects on *B. bassiana*-colonized plants. Although it has never been substantiated in any detail so far, this speculation might explain the virulence of endophytic *B. bassiana* against *H. armigera* when direct parasitism is not evident. *B. bassiana* is known to produce several low-molecular-weight secondary metabolites (e.g. beauvericin, beauverolides, enniatins, bassianolide, bassianolone, bassiatin, oosporein, cyclosporine A, and oxalic acid) that display a wide array of insecticidal, antibacterial, antifungal, and cytotoxic activities. However, in planta production of any of these *B. bassiana*-derived secondary metabolites is a largely untapped area of research that definitely warrants investigation.

Although *B. bassiana*-based biopesticides have been tested for *H. armigera* management, abiotic factors (rainfall, humidity, temperature, and sunlight) and biotic factors (rhizosphere and phyllosphere microbial competitors) render the current field delivery methods of conventional *B. bassiana* biopesticides impractical. Introducing *B. bassiana* into plants as an artificial endophyte could circumvent such problems and offer a promising alternative delivery method of the fungus for the effective management of *H. armigera*. Endophytic *B. bassiana* could be directly used to treat seeds or transplants, thus limiting substantially the side-effects of abiotic and biotic factors on the fungus by almost immediately protecting it within plant tissues. Besides, treatment with endophytic *B. bassiana* may only require little inoculum; drastically reducing application costs. Furthermore, given that *B. bassiana* is a generalist pathogen with no strict host preference; it is not a great intuitive leap to suppose that selecting a virulent isolate/strain capable of extensive endophytic colonization of a certain host plant would be sufficient to deal with most of its insect and pathogen pests.

TABLE 1

Height and weight of *sorghum* plants treated with *B. bassiana* as affected by inoculation method and plant growth medium (vermiculite, non-sterile soil, or sterile soil, respectively)

| Inoculation Method | Shoot height (cm) | Root length (cm) | Fresh shoot weight (g) | Fresh root weight (g) | Dry shoot weight (g) | Dry root weight (g) |
|---|---|---|---|---|---|---|
| Vermiculite | | | | | | |
| Seed | 22.0 ± 0.7a | 20.6 ± 0.6a | 0.42 ± 0.01a | 0.86 ± 0.02a | 0.12 ± 0.01a | 0.14 ± 0.01a |
| Leaf | 22.1 ± 0.7a | 22.4 ± 0.4a | 0.46 ± 0.05a | 0.85 ± 0.02a | 0.12 ± 0.02a | 0.15 ± 0.01a |
| Soil | 22.1 ± 0.7a | 22.0 ± 0.8a | 0.40 ± 0.09a | 0.86 ± 0.02a | 0.11 ± 0.02a | 0.17 ± 0.06a |
| Control | 21.4 ± 0.3a | 21.4 ± 0.6a | 0.39 ± 0.07a | 0.84 ± 0.03a | 0.11 ± 0.01a | 0.13 ± 0.03a |

TABLE 1-continued

Height and weight of *sorghum* plants treated with *B. bassiana* as affected by inoculation method and plant growth medium (vermiculite, non-sterile soil, or sterile soil, respectively)

| Inoculation Method | Shoot height (cm) | Root length (cm) | Fresh shoot weight (g) | Fresh root weight (g) | Dry shoot weight (g) | Dry root weight (g) |
|---|---|---|---|---|---|---|
| Sterile soil | | | | | | |
| Seed | 70.7 ± 0.6a | 23.3 ± 0.8a | 7.1 ± 0.2a | 2.6 ± 0.4a | 1.2 ± 0.02a | 0.31 ± 0.04a |
| Leaf | 69.3 ± 0.4a | 21.6 ± 0.4a | 6.8 ± 0.1a | 2.8 ± 0.1a | 1.2 ± 0.02a | 0.34 ± 0.03a |
| Soil | 70.9 ± 0.7a | 21.6 ± 0.7a | 7.5 ± 0.1a | 2.6 ± 0.4a | 1.2 ± 0.02a | 0.39 ± 0.03a |
| Control | 70.1 ± 0.5a | 21.5 ± 0.5a | 7.6 ± 0.1a | 2.7 ± 0.1a | 1.1 ± 0.02a | 0.46 ± 0.02a |
| Non-sterile soil | | | | | | |
| Seed | 60.8 ± 0.8 | 31 ± 1.7a | 6.6 ± 0.2a | 2.5 ± 0.05a | 0.58 ± 0.03a | 0.13 ± 0.01a |
| Leaf | 62.1 ± 1.6a | 31.8 ± 19a | 7.2 ± 0.3a | 2.5 ± 0.08a | 0.49 ± 0.03a | 0.14 ± 0.04a |
| Soil | 58.7 ± 1.5a | 34.9 ± 1.7a | 6.7 ± 0.3a | 2.4 ± 0.07a | 0.50 ± 0.04a | 0.15 ± 0.01a |
| Control | 62.2 ± 1.1 | 31.7 ± 1.7a | 6.5 ± 0.2a | 2.6 ± 0.05a | 0.51 ± 0.05a | 0.17 ± 0.01a |

For each growth medium, means (±SE) followed by the same letter within a column are not significantly different at $P < 0.05$

The invention claimed is:

1. A method for pest control comprising inoculating plants, parts of plants or the surroundings of said plants with an effective amount of isolated endophytic *Beauveria bassiana* strain ATP02, DSM 24665.

2. A method for treating or preventing plants against pest infestation comprising the step of inoculating said plants, parts of said plants or the surroundings of said plants with an effective amount of isolated endophytic *Beauveria bassiana* strain ATP02, DSM 24665.

3. The method according to claim 1 wherein the plant, parts of plants or the surroundings of said plants is selected from leaf, seed, soil, stems, branches, and roots.

4. The method according to claim 1, wherein the plants are crops.

5. The method according to claim 1, wherein the plants are crops selected from *Vicia faba*, rapeseed, chickpea, maize, sorghum, broad bean, cotton, tobacco, soy, banana, coffee, tomato, cocoa plants, cabbage, corn, bean, potato, opium poppy, date palm, pine, wheat, rice, cereals, and barley.

6. The method according to claim 1, wherein the plants are selected from rapeseed, *Brassica napus*, cotton, maize, corn, and soy.

7. The method according to claim 1, comprising the step of coating seeds or inoculating seeds of said plants with an effective amount of the isolated endophytic *Beauveria bassiana* strain ATP02, DSM 24665.

8. The method according to claim 1, wherein the pests are insects.

9. The method according to claim 1, wherein the pests are insects selected from herbivorous insects and plant pathogens.

10. A bio-pesticide containing an effective amount of isolated endophytic *Beauveria bassiana* strain ATP02 (DSM 24665).

11. A composition containing an effective amount of isolated endophytic *Beauveria bassiana strain ATP*02, DSM 24665, as an active component for pest control.

12. The composition according to claim 11, wherein said composition is in a form selected from a solution, a dispersion, spore suspension, sclerotia, emulsion, gel, layer, cream, coating, dip, encapsulated or granule.

13. A method of endophytically colonizing plants comprising the steps of inoculating said plants or parts of said plants or surroundings of said plants with an effective amount of isolated *Beauveria bassinana* strain ATP02, DSM 24665 sufficient to cause endophytic colonization of said plants or said parts of said plants or said surroundings of said plants.

14. The method according to claim 13 wherein said plants are selected from the group consisting of *Vicia faba*, maize, corn, broad bean, sorghum, tobacco, rapeseed, soy, chickpea, cotton, banana, coffee, tomato, cocoa, cabbage, bean, potato, opium poppy, date palm, pine, wheat, rice, cereals, and barley plants.

15. The method of claim 9, wherein said herbivorous insects and plant pathogens are selected from *Helicoverpa armigera, Spodoptera* spp., *Trialeurodes vaporariorum*, and *Plutella xylostella.*

16. The composition of claim 11, wherein said pests are herbivorous insects and/or plant pathogens.

17. The method of claim 1, wherein said parts of plants are seeds, and said isolated endophytic *Beauveria bassiana* strain ATP01, DSM 24665 is in the form of conidia.

18. The method of claim 13, wherein said parts of plants are seeds, and said isolated endophytic *Beauveria bassiana* strain ATP01, DSM 24665 is in the form of conidia.

* * * * *